United States Patent [19]

Griffin

[11] 4,367,961
[45] Jan. 11, 1983

[54] THERMAL MEASURING APPARATUS FOR ELASTOMERS

[75] Inventor: Warren R. Griffin, Kettering, Ohio

[73] Assignee: The United States of America as represented by the Secretary of the Air Force, Washington, D.C.

[21] Appl. No.: 221,185

[22] Filed: Dec. 30, 1980

[51] Int. Cl.³ .......................... G01N 3/24; G01N 3/18
[52] U.S. Cl. ........................................ 374/46; 73/835
[58] Field of Search ................. 73/15 R, 15.6, 17 R, 73/81, 835, 841, 159

[56] References Cited

U.S. PATENT DOCUMENTS

| | | | |
|---|---|---|---|
| 1,836,621 | 12/1931 | Schubert | 73/835 |
| 2,495,746 | 1/1950 | Lubin | 73/15.6 |
| 3,187,556 | 6/1965 | Ehlers | 73/17 |
| 3,319,462 | 5/1967 | Ostrowski | 73/835 |
| 3,350,917 | 11/1967 | Wincklhofer et al. | 73/15.6 |
| 3,369,391 | 2/1968 | Warfield | 73/17 |
| 3,581,558 | 6/1971 | Porter | 73/101 |
| 3,599,476 | 8/1971 | Corbett | 73/15.6 |
| 3,611,787 | 10/1971 | D'Annessa et al. | 73/15.6 |
| 3,693,421 | 9/1972 | Karper | 73/101 |
| 3,774,440 | 11/1973 | Martinelli | 73/15.6 |
| 3,785,201 | 1/1974 | Robio et al. | 73/81 |
| 3,788,135 | 1/1974 | Hammond, Jr. | 73/15 |
| 3,813,919 | 6/1974 | Taniguchi et al. | 73/15.6 |
| 3,818,751 | 6/1974 | Karper | 73/15.6 |
| 4,019,365 | 4/1977 | Woo | 73/15.6 |
| 4,114,420 | 9/1978 | Browning | 73/15.6 |
| 4,145,912 | 3/1979 | Hognat et al. | 73/15.6 |

OTHER PUBLICATIONS

Gent. A. N. et al., "Tear Strength of Stetched Rubber," *Rubber Chemistry and Technology*, vol. 51, pp. 35–44.
PPT Tear Tester, Testing Machines, Inc., Mineola, N.Y.

*Primary Examiner*—Herbert Goldstein
*Attorney, Agent, or Firm*—Donald J. Singer; Jacob N. Erlich

[57] ABSTRACT

An apparatus for measuring the tear strength of an elastomer specimen having a housing which contains therein a specimen holder, a controllable heat source, a force applying assembly which includes a taut wire, means for measuring the amount of movement of the force applying assembly and a temperature programmer and strip chart recorder. The force applying assembly by means of the taut wire applies a predetermined amount of force on the elastomer specimen which has been precut on one side thereof. The load on the taut wire is counterbalanced by a calibrated spring such that the load decreases linearly to zero as the tearing of the specimen is completed. The result of the tearing is displayed and shows the transition of the elastomer from glass to rubber, the modulus before tearing, the progression of tearing versus increasing temperature, and the strength of the elastomer at elevated temperatures.

1 Claims, 6 Drawing Figures

THERMAL MEASURING APPARATUS FOR ELASTOMERS

STATEMENT OF GOVERNMENT INTEREST

The invention described herein may be manufactured and used by or for the Government for governmental purposes without the payment of any royalty thereon.

BACKGROUND OF THE INVENTION

This invention relates generally to an apparatus for testing the tear strength of elastomers, and, more particularly to an apparatus that is capable of measuring the tear strength or toughness of a crosslinked elastomeric polymer over the useful temperature range of the elastomer.

In the manufacture of products made from elastomeric material, it is important to know as much as possible about the pertinent physical properties of the material in order to knowledgeably control the manufacture of the finished product. For example, it is well recognized that a problem of temporary loss of tensile strength of elastomers can result at high temperatures. More specifically, tensile properties of oil resistant elastomers decrease from approximately 3000 psi at room temperature to 300 to 400 psi at 350° F. When cooled, the elastomers again become tough and strong. The general conclusion reached is that this effect is present with all visco-elastic materials and can generally be predicted from knowing the glass to rubber transistion temperature of the elastomer.

There have also been, however, abnormalities observed such as improved high temperature strength with the utilization of highly reinforcing fillers, high crosslink density and very high molecular weight, linear polymers. In fact, block copolymers have recently been prepared which hold the promise of maintaining strength properties to a higher temperature before severe loss occurs.

By providing an apparatus which is capable of measuring tear propagation in elastomers as a continuous function of temperature it would be possible to set such test equipment at values of temperature which correspond to, for example, systems such as hydraulic systems which incorporate elastomers therein. Thus, it would be possible to select elastomer formulations that were likely to be more durable in such applications.

Unfortunately, through the years the equipment utilized for investigating the properties of elastomers have remained substantially unchanged. Tensile measurements at various temperatures generally require considerable effort and a large number of samples. In many instances, cold and hot tear measurements were conducted which paralleled the tensile loss. This necessitated several specimens at each of several temperatures and therefore required much time and material. Furthermore, prior test equipment had inadequate provisions for temperature control. In addition, in many instances such test equipment was unable to differentiate between soft tough material and those that were of high hardness with poor strength properties. Consequently, there is an urgent need for a simple apparatus than can indicate ultimate tensile strength of elastomers on microspecimens, at various temperatures, and which is capable of measuring such properties independent of occasional flaws in the sample.

SUMMARY OF THE INVENTION

The instant invention overcomes the problems encountered in the past by providing an apparatus which is capable of measuring tear strength or toughness in an elastomeric specimen as a continuous function of temperature and thereby provide data on the whole elastomeric range of the specimen (from glass temperature to thermal decomposition) during a single operation and with a single sample weighing less than 0.2 grams.

The tear measuring apparatus of this invention is made up of a housing which contains therein a controllable heat source, a uniquely designed mount for a microsized elastomer sample or specimen, a force applying assembly which includes a taut wire element, means for viewing the testing of the elastomer, means for measuring the amount of movement of the force applying assembly, and a temperature programmer and strip chart recorder for registering appropriate data on the tear strength of the elastomer versus temperature.

The apparatus of this invention employs a minutely sized elastomer specimen which has been precut from one surface thereof to leave an extremely small (approximately 0.2 mm) web of uncut elastomer. During use of the tear measuring apparatus of this invention the web of elastomer is strained by the taut wire of the force applying assembly at a programmed stress level as the temperature within the housing and therefore on the elastomer specimen increases between the −100° C. and +300° C. range. The web is strained by the taut wire as the elastomer specimen is held at approximately a 60° angle within a holder of the test apparatus. A load is applied to the wire which is counter balanced linearly to zero as the tear progresses through the specimen. A strip chart recorder displays the glass to rubber transition and a non-linear progression of tearing of the elastomer specimen with linear temperature increase.

It is therefore an object of this invention to provide an apparatus for measuring the toughness or tear strength of a crosslinked elastomer specimen as a function of temperature.

It is another object of this invention to provide a tear measuring for elastomers capable of recording the resultant data obtained during the test procedure.

It is a further object of this invention to provide a tear measuring apparatus for elastomers which is capable of determining the useful elastomeric range of experimental polymers in a quick and reliable procedure with a less than one gram elastomer specimen.

It is still a further object of this invention to provide a tear measuring apparatus for elastomers which is economical to produce and which utilizes conventional, currently available components that lend themselves to standard mass producing manufacturing techniques.

For a better understanding of the present invention together with other and further objects thereof, reference is made to the following description taken in conjunction with the accompanying drawing and its scope will be pointed out in the appended claims.

DETAILED DESCRIPTION OF THE DRAWING

DETAILED DESCRIPTION OF THE PREFERRED EMBODIMENTS

Figure 1:
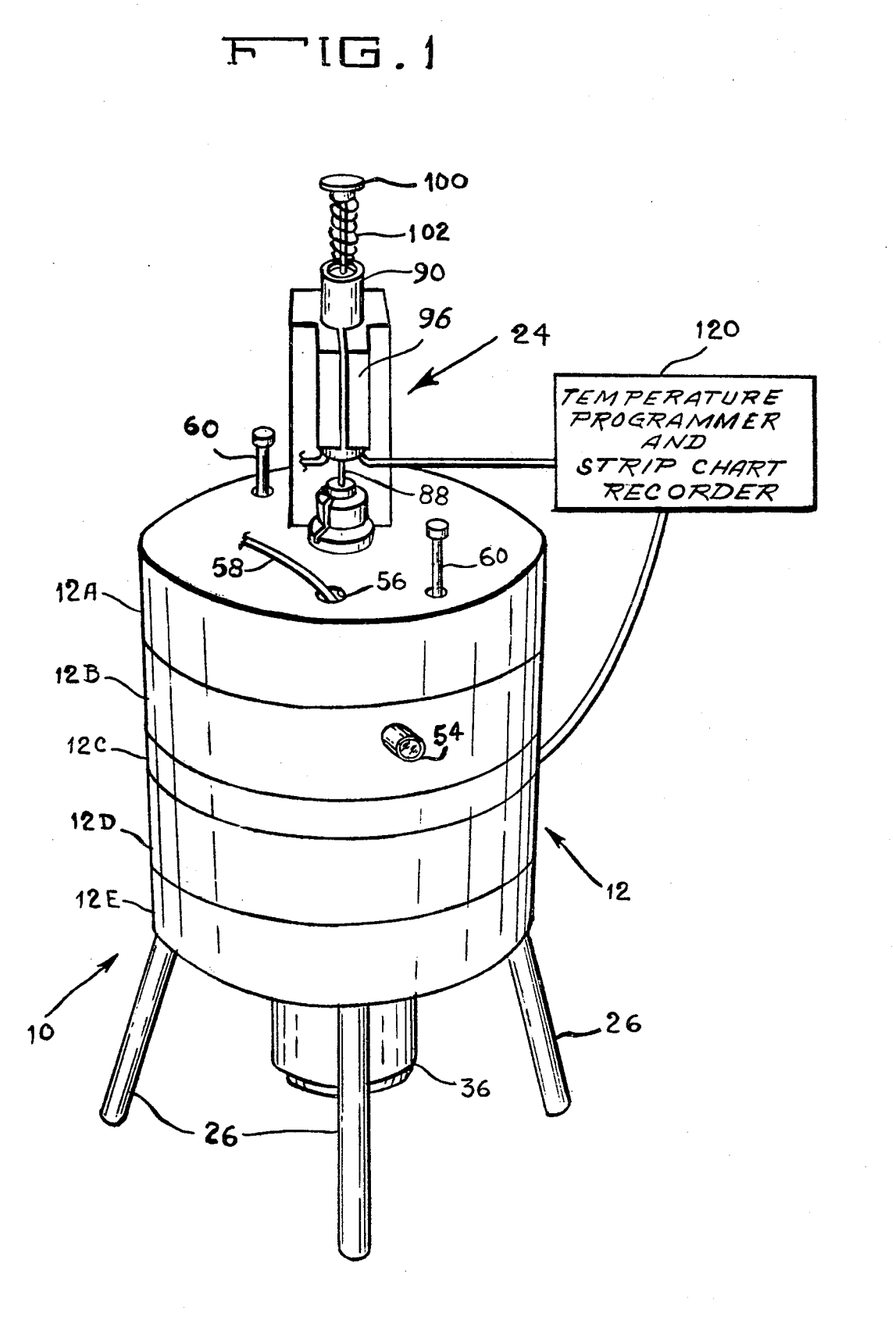
FIG. 1 is a pictorial representation of the tear measuring apparatus for elastomers of this invention.
Figure 2:
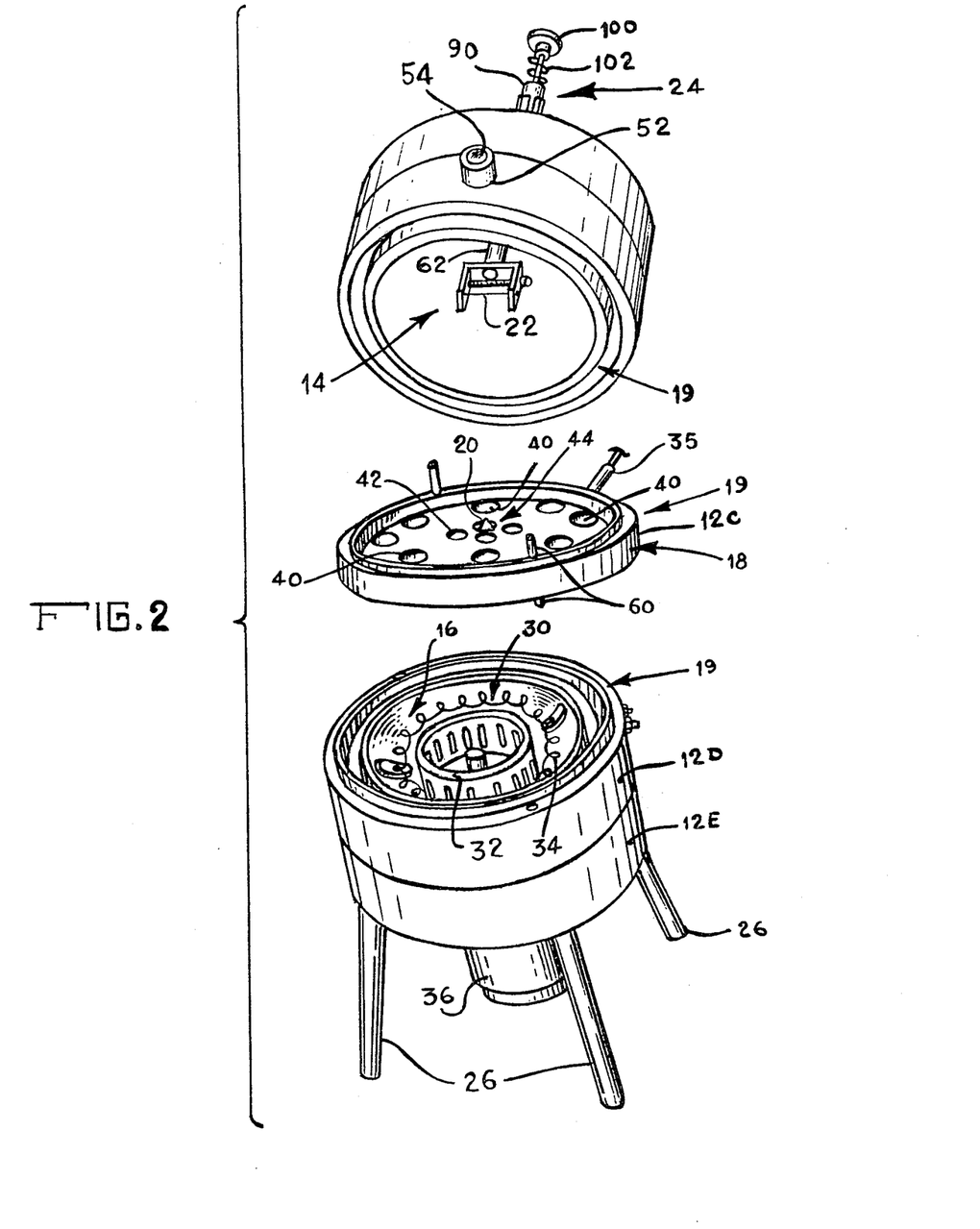
FIG. 2 is a pictorial representation of the tear measuring apparatus for elastomers of this invention and shown in exploded fashion.

Reference is now made to FIGS. 1 and 2 of the drawing which clearly show in pictorial fashion the various elements which make up the tear measuring apparatus for elastomers 10 of this invention. The tear measuring apparatus 10 is made up of a housing 12 formed of a plurality of disk-shaped elements 12A–12E made of any suitable insulating substance such as asbestos or ceramic material. A thin specimen or sample of vulcanized elastomer 20, to be described in detail hereinbelow, can be precisely controlled in temperature within the insulated housing 12 while a taut wire 22 formed as part of a force applying assembly 24 also described in detail hereinbelow causes the elastomer specimen 20 to undergo tearing.

Still referring to FIG. 2 of the drawing a more specific description of housing 12 of the tear measuring apparatus 10 of this invention is now set forth. A lower chamber 16 is formed within elements 12D and 12E and can be stably mounted upon any flat surface (not shown) by the utilization of a plurality of supporting legs 26 which extend from disc-shaped element 12E. Lower chamber 16 can be of any suitable configuration but is preferably concave in shape so as to rigidly support therein the heating mechanism 30 of tear apparatus 10 of this invention. Heating mechanism 30 includes a conventional centrally located motor driven fan 32 surrounded by a heating coil 34. The motor 36 which drives fan 32 may be an integral part of fan 32 or may be located external of the lower chamber 16 as shown and be operably connected to fan 32 through element 12E. In this manner, by connecting heating element 34 to an appropriate electrical power source (not shown) and a conventional thermocouple 35 which is operably connected to disc-shaped element 12C, activation of motor 36 and fan 32 will cause heated air to flow along the outer edges of the concave lower chamber 16. Deenergizing of heating element 34 permits the flow of unheated air from lower chamber 16.

Attention is now directed to disc-shaped element 12C which constitutes dividing plate 18. Dividing plate 18 has a substantially flat surface which contains therein a plurality circumferentially located openings 40 adjacent the outer edge thereof. A smaller number of openings 42 are situated circumferentially about the center of dividing plate 18. Located directly at the center of dividing plate 18 is a specimen holder 44 for mounting the elastomer specimen 20 in a manner which is described in detail hereinbelow with respect to FIG. 5. The temperature of specimen 20 can be sensed by thermocouple 35. Consequently, the activation and deactivation of heating coil 34 can be regulated by thermocouple 35.

Upper chamber 14 is also preferably of a concave configuration formed within elements 12A and 12B. In addition, upper chamber 14 has a centrally located aperture 50 therein (shown in FIG. 3 of the drawing) which allows for the protrusion therethrough of the operating portion of the force applying assembly 24. The details of the force applying assembly 24 will be set forth hereinbelow with reference to FIGS. 3 and 4 of the drawing. Also, situated in optical alignment with upper chamber 14 and in disc-shaped element 12B is a radially extending viewing aperture 52 and a removable magnifying sight glass 54. Sight glass 54 can be utilized in viewing the tearing operation undergone by the elastomer specimen 20 during testing by apparatus 10 of this invention. Furthermore, as shown in FIG. 1 of the drawing, upper chamber 14 has an opening 56 extending through elements 12A and 12B for purposes of allowing any suitable conventional lighting device 58 to be lowered into the concave chamber 14. Aperture 56 can also be utilized as a vent for escaping gases which can pass therethrough during the testing procedure. A pair of alignment rods 60 can be utilized to secure the various elements 12A–12E of housing 12 in appropriate registration.

Figure 3:
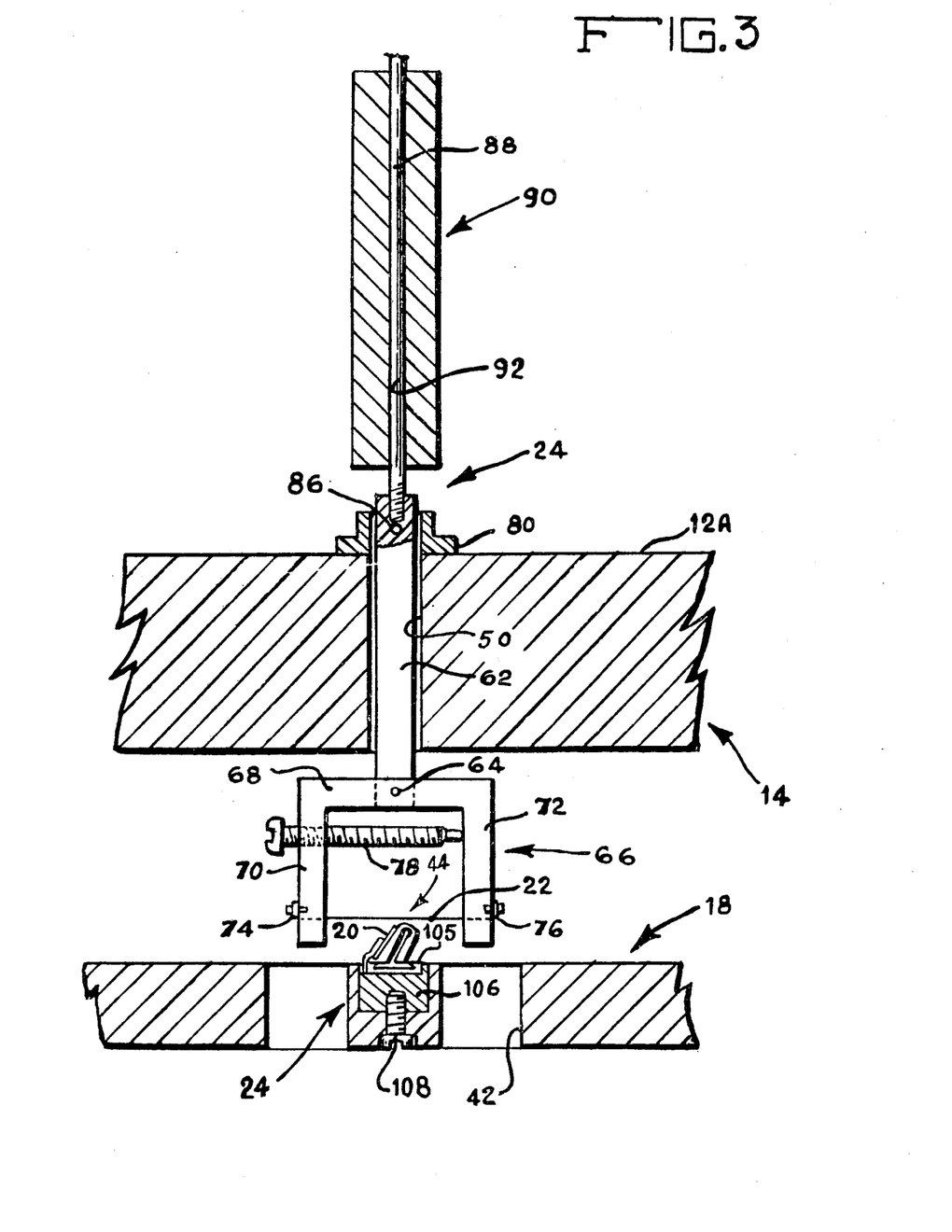
FIG. 3 is a side-elevational view, showing specifically the force applying assembly, of the tear measuring apparatus for elastomers of this invention and illustrated partly in cross-section.
Figure 4:
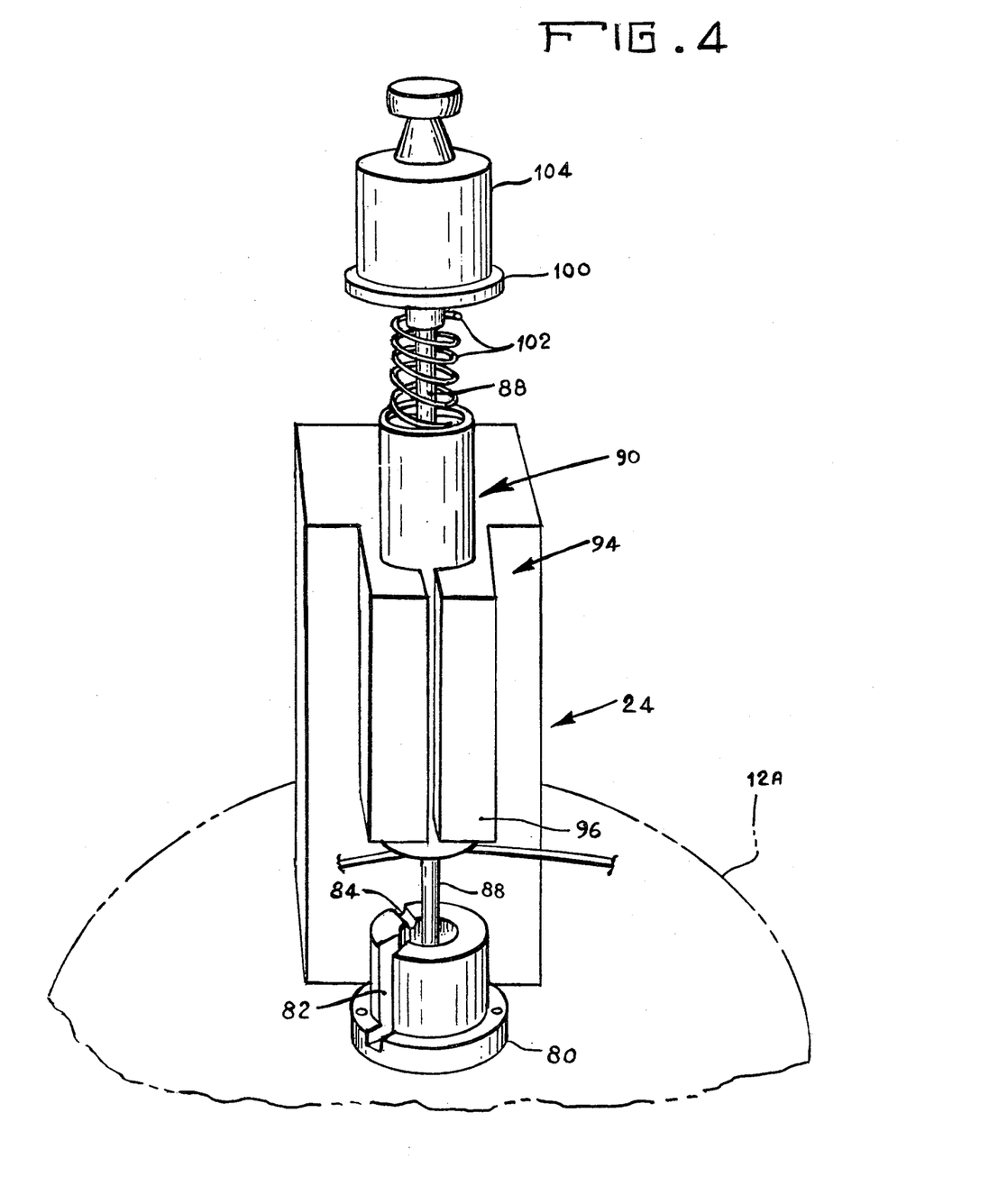
FIG. 4 is a pictorial representation of the transducer utilized with tear measuring apparatus for elastomers of this invention.

As stated hereinabove reference is now made to FIGS. 3 through 5 in which the force applying assembly 24 and the specimen holder 44 are described in detail. Referring to FIGS. 3 and 4 of the drawing the force applying assembly 24 is illustrated as being made up of a rod 62 of any suitable material such as asbestos which passes through aperture 50 located in upper chamber 14. Secured to the lower end of rod 62 by any suitable securing means such as a pin 64 is a yoke arrangement 66. Yoke arrangement 66 is made up of an inverted U-shaped configured element having a base 68 and a pair of outstanding legs 70 and 72. The taut wire 22 is located between and secured to opposed legs 70 and 72 of yoke arrangement 66. Any suitable fastening element such as mounting screws 74 and 76 are utilized to fixedly secure wire 22 to legs 70 and 72. The appropriate tension can be applied to wire 22 by means of a threaded bolt 78 screwed through one of the legs 70 and which abuts the other leg 72.

A collar 80 is mounted on the upper portion of disc-shaped element 12A and has a pair of slots 82 and 84 situated vertically therein. One of the slots 82 goes substantially completely through collar 80 to allow for the passing therethrough of a pin 86 (see FIG. 3) extending from the upper end of rod 62. The other slot 84 is in the form of an identation in collar 80 and when in registration with pin 86 prevents the force applying assembly 24 to be lowered through aperture 50. Consequently, wire 22 has two positions, one in which it is out of engagement with specimen 20 (in which pin 86 is situated in slot 84) and another in which it is capable of engaging specimen 20 (in which pin 86 is situated in slot 82). Also secured to the upper end of rod 62 is elongated extension rod element 88 which is utilized as part of a linear movement detector such as linear transducer 90. Elongated element 88 passes through in slidable fashion a centrally located opening 92 in linear transducer 90.

Linear transducer 90 as illustrated in FIG. 4 of the drawing is fixedly secured with respect to housing 12 by means of a transducer mounting block 94. Transducer mounting block 94 incorporates therein a clamping element 96 which fixedly secures transducer 90 therein. Completely the force applying assembly 24 is a receiving means for selected weights in the form of weight pan 100 and a calibrated spring 102 surrounding element 88 and interposed between weight pan 100 and the top of transducer 90. Spring 102 is calibrated such that upon the application of any suitable weight 104 such as 100 grams upon weight pan 100, spring 102 will counterbalance weight 104 as yoke 66 and therefore wire 22 completes its pass through specimen 20 in a manner described in detail hereinbelow.

Figure 5:
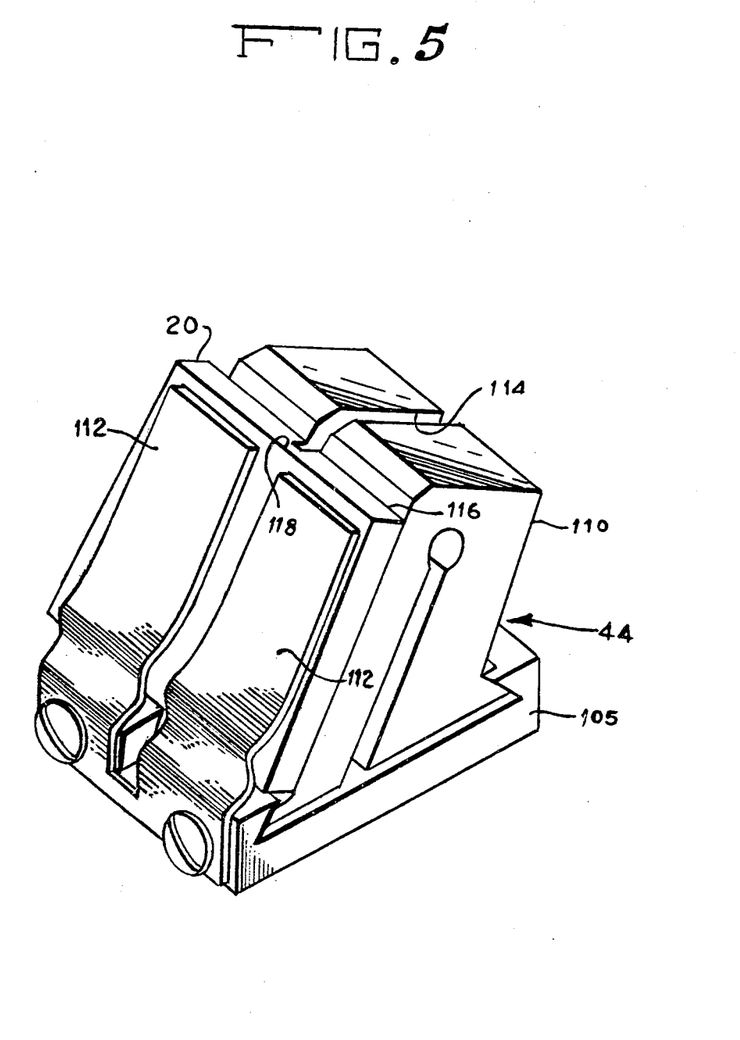
FIG. 5 is a pictorial representation of the elastomer specimen or sample holder utilized with the tear measuring apparatus for elastomers of this invention.

Reference is now made to FIG. 5 of the drawing which shows in pictorial fashion specimen holder 44 which can be utilized with the tear measuring apparatus 10 of this invention. Holder 44 has a base plate 105 which is mounted in a body 106 rotatably secured to the central portion of dividing plate 18 by means of any suitable securing element such as bolt 108 (see FIG. 3). Secured in base plate 105 is a back support 110 which protrudes from base plate 105 at approximately 60° to 80° (preferably 60°) from the vertical. Back support 110 is utilized in conjunction with a pair of spring bias elements 112 to support the elastomer specimen 20 therebetween. A slot 114 is formed within back support 110 so as to accommodate wire 22 as it passes through specimen 20 during the testing procedure.

As shown in FIG. 5 of the drawing, the elastomer specimen 20 is preferably a square element approximatey 12.7 mm by 12.7 mm by 2 mm in width and has been precut at one surface 116 thereof to leave a small web 118 of material approximately 0.2 mm thick. This web 118 of uncut elastomer is to be cut by wire 22 during the test operation performed by the tear measuring apparatus 10 of this invention.

Figure 6:
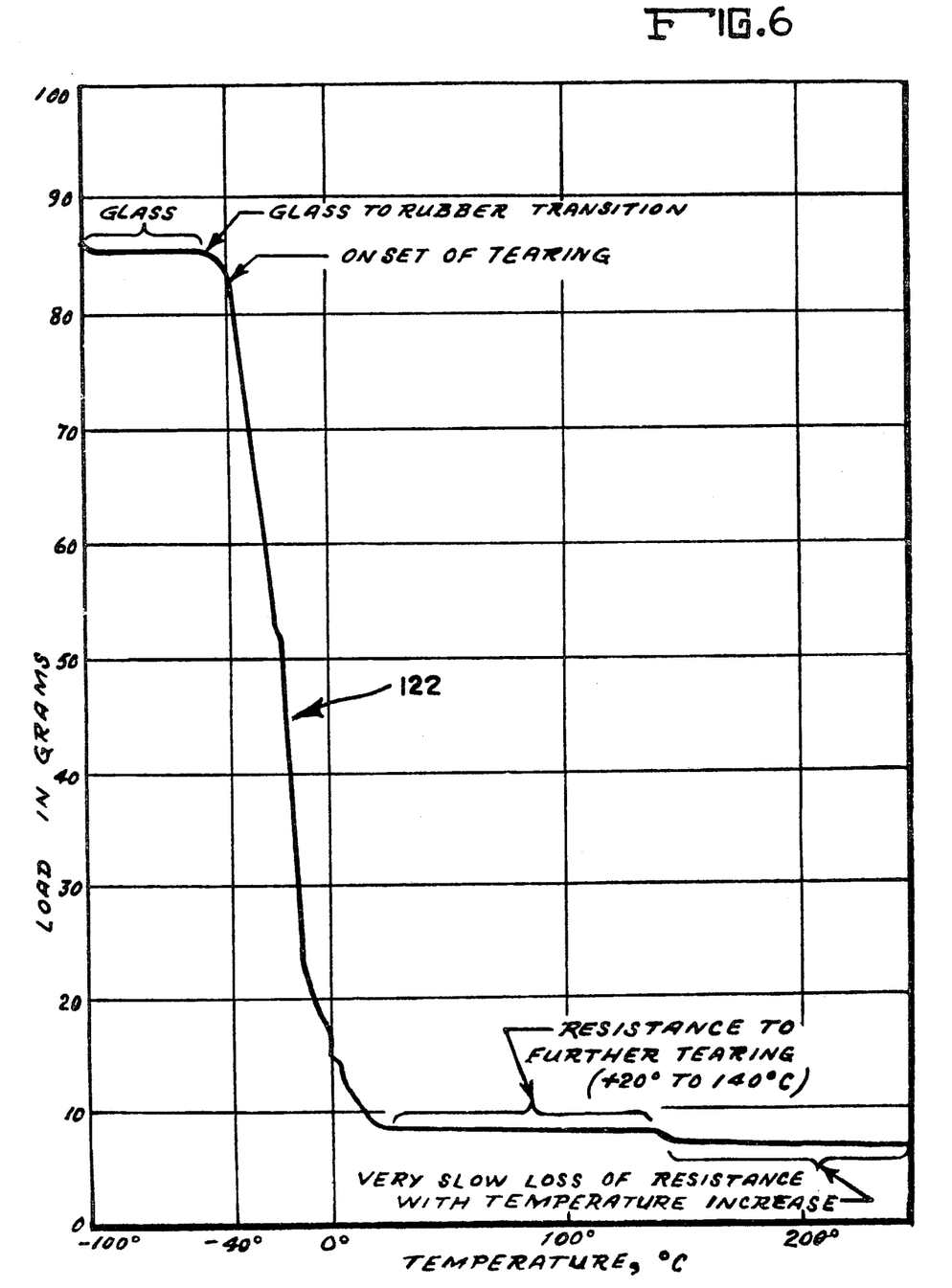
FIG. 6 is a graphic representation of a thermal tear analysis performed by the tear measuring apparatus for elastomers of this invention.

Data received from the transducer 90 and thermocouple 35 is input to a conventional temperature programmer and strip chart recorder 120 such as a Columbia Scientific Instruments Programmer/Recorder LB202. In this manner, a thermal tear analysis of an elastomer specimen 20 can be made by comparing resistance of the elastomer to the force applied thereto as a function of temperature. A graph 122 representative of loading grams versus temperature is shown in FIG. 6 of the drawing. The temperature of specimen 20 is controlled in a conventional manner by inputs from the thermocouple 35.

MODE OF OPERATION

Operation of the tear measuring apparatus 10 of this invention begins with the insertion of a suitable elastomer specimen 20 therein. Therefore, the force applying assembly 24 should be raised to its nonoperational position by rotating rod 62 such that pin 86 engages the upper surface of slot 84. Thereafter, elements 12A and 12B forming upper chamber 14 are lifted by means of threaded rods 60 to allow access to specimen holder 44 on divider plate 18. Testing begins by inserting within specimen holder 44 a prepared specimen 20 of elastomer material (preferably 12.7 mm by 12.7 mm by 2 mm and weighing approximately 0.2 grams) which has been precut from one surface thereof to leave an approximately 0.2 mm web 18 of uncut elastomer. Thereafter, elements 12A and 12B forming upper chamber 14 are placed upon the dividing plate 18 so as to form the completed housing 12 of apparatus 10 as shown in FIG. 1 of the drawing. The appropriate alignment between the specimen 20 and the wire 22 of yoke 66 can be made prior to combining elements 12A-12E by appropriate rotation of holder body 106 within plate 18. Visual inspection of the orientation can be made through sight glass 54. Temporary illumination is accomplished by the insertion of lighting device 58 through aperature 56 in elements 12A and 12B.

Apparatus 10 is then cooled to liquid nitrogen ($LN_2$) temperature by pouring $LN_2$ into the sight glass aperture 52 through a conventional fluorocarbon adapter (not shown) while circulating the gas with the movement of fan 32 by the activation of motor 36. Thereafter rod 62 is rotated so as to lift it from slot 84 such that pin 86 is now aligned with slot 82. Wire 22 can now be lowered to contact specimen 20 by the application of appropriate weights 104 on weight pan 100. The movement of wire 22 through specimen 20 can be recorded as the specimen is heated at a rate of, for example, 1° C./minute by heating element or coil 34.

The web 118 of specimen 20 is strained by the wire 22 which is taut and at an angle of approximately 60° with respect to the vertical while a force in the form of, for example, a 100 gram load is situated on weight pan 100. This 100 gram load is counter balanced linearly to zero as the tear progresses through specimen 20 by spring 102. Strip chart recorder 120 displays the glass to rubber transition and a non-linear progression of tearing with linear temperature increase. The thermocouple 35 measures the temperature of dividing plate 18 (and thereby specimen 20) and inputs this information to the temperature programmer for heater control. As illustrated in FIG. 6 of the drawing, the glass to rubber transition of an elastomer specimen can be seen, as well as the onset of tearing which takes place between approximately −40° C. until substantial resistance to further tearing occurs between approximately 20° to 140° C. It is therefore possible with the tear measuring apparatus 10 of this invention to reliably measure tear strength as a continuous function of temperature, during a single test procedure, and with a microsized specimen weighing less then 0.2 grams.

Although this invention has been described with reference to a particular embodiment, it will be understood to those skilled in the art that this invention is also capable of further and other embodiments within the spirit and scope of the appended claims.

I claim:

1. An apparatus for measuring the tear strength of an elastomer specimen comprising a housing; means situated within said housing for fixedly supporting said elastomer specimen; means situated within said housing in operable relationship to said elastomer specimen for applying a predetermined amount of force to said elastomer specimen, said force applying means including a movable element, a thin wire secured to one end of said movable element, and means secured to the other end of said movable element for applying a preselected amount of load on said movable element; means operably connected to said housing for controlling the temperature of said elastomer specimen; and means connected to said force applying means for determining the resistance of said elastomer specimen to the application of said predetermined force whereby upon the application of said load on said movable element said thin wire is capable of passing through said elastomer specimen and said tear strength of said elastomer can be measured with respect to a variation in the temperature of said elastomer specimen.

2. An apparatus for measuring the tear strength of an elastomer specimen as defined in claim 1 wherein said means for controlling the temperature of said elastomer specimen comprises a heating element and means for selectively controlling the amount of heat generated by said heating element.

3. An apparatus for measuring the tear strength of an elastomer specimen as defined in claim 1 wherein said means for determining the resistance of said elastomer specimen comprises means for measuring the amount of movement of said movable element as said thin wire passes through said elastomer specimen.

4. An apparatus for measuring the tear strength of an elastomer specimen as defined in claim 3 wherein said force applying means further comprises means connected to said housing for supporting said movement measuring means and said movable element being slidably connected to said movement measuring means.

5. An apparatus for measuring the tear strength of an elastomer specimen as defined in claim 4 wherein said force applying means further comprises means operably connected to said load applying means for applying a linearly increasing counterbalancing force to said load applying means.

6. An apparatus for measuring the tear strength of an elastomer specimen as defined in claim 3 wherein said means for controlling the temperature of said elastomer specimen comprises a heating element and means for selectively controlling the amount of heat generated by said heating element.

7. An apparatus for measuring the tear strength of an elastomer specimen as defined in claim 6 wherein said force applying means further comprises means connected to said housing for supporting said movement measuring means and said movable element being slidably connected to said movement measuring means.

8. An apparatus for measuring the tear strength of an elastomer specimen as defined in claim 7 wherein said force applying means further comprises means operably connected to said load applying means for applying a linearly increasing counterbalancing force to said load applying means.

9. An apparatus for measuring the tear strength of an elastomer specimen as defined in claim 8 wherein said means for fixedly supporting said elastomer specimen comprises a support plate, means for fixedly holding said elastomer specimen at a preselected angle with respect to said force applying means, and means interconnected between said support plate and said elastomer specimen holding means for rotatably securing said elastomer specimen holding means to said support plate in order to appropriately adjust the position of said elastomer specimen with respect to said force applying means.

10. An apparatus for measuring the tear strength of an elastomer specimen as defined in claim 9 wherein said support plate contains a plurality of openings therein for allowing said heat generated by said heating element to pass therethrough.

11. An apparatus for measuring the tear strength of an elastomer specimen as defined in claim 1 further comprising means within said housing through which said elastomer specimen can be viewed.

12. An apparatus for measuring the tear strength of an elastomer specimen as defined in claim 1 wherein said force applying means further comprises a yoke-shaped element, one end of said yoke-shaped element being fixedly secured to said one end of said movable element, and said wire being secured to said yoke-shaped element.

13. An apparatus for measuring the tear strength of an elastomer specimen as defined in claim 12 wherein said yoke-shaped element includes means for applying a predetermined amount of tension to said wire.

14. An apparatus for measuring the tear strength of an elastomer specimen comprising a housing; means situated within said housing in operable relationship to said elastomer specimen for applying a predetermined amount of force to said elastomer specimen; means situated within said housing for fixedly supporting said elastomer specimen, said means for fixedly supporting said elastomer specimen including a support plate, means for fixedly holding said elastomer specimen at a preselected angle with respect to said force applying means, and means interconnected between said support plate and said elastomer specimen holding means for rotatably securing said elastomer specimen holding means to said support plate in order to appropriately adjust the position of said elastomer specimen with respect to said force applying means; means operably connected to said housing for controlling the temperature of said elastomer specimen, said temperature controlling means including a heating element and means for selectively controlling the amount of heat generated by said heating element; and means connected to said force applying means for determining the resistance of said elastomer specimen to the application of said predetermined force whereby said tear strength of said elastomer can be measured with respect to a variation in the temperature of said elastomer specimen.

15. An apparatus for measuring the tear strength of an elastomer specimen as defined in claim 14 wherein said support plate contains a plurality of openings therein for allowing said heat generated by said heating element to pass therethrough.

16. An apparatus for measuring the tear strength of an elastomer specimen comprising a housing; means situated within said housing in operable relationship to said elastomer specimen for applying a predetermined amount of force to said elastomer specimen; means situated within said housing for fixedly supporting said elastomer specimen, said means for fixedly supporting said elastomer specimen including a support plate, means for fixedly holding said elastomer specimen at a preselected angle with respect to said force applying means, and means interconnected between said support plate and said elastomer specimen holding means for rotatably securing said elastomer specimen holding means to said support plate in order to appropriately adjust the position of said elastomer specimen with respect to said force applying means; means operably connected to said housing for controlling the temperature of said elastomer specimen; and means connected to said force applying means for determining the resistance of said elastomer specimen to the application of said predetermined force whereby said tear strength of said elastomer can be measured with respect to a variation in the temperature of said elastomer specimen.

17. An apparatus for measuring the tear strength of an elastomer specimen as defined in claim 16 wherein said specimen holding means comprises a base plate and a back support which protrudes from said base plate at said predetermined angle.

18. An apparatus for measuring the tear strength of an elastomer specimen as defined in claim 17 wherein said force applying means comprises a movable element, a thin wire secured to one end of said movable element, and means secured to the other end of said movable element for applying a preselected amount of load on said movable element whereby upon the application of said load on said movable element said thin wire is capable of passing through said elastomer specimen.

19. An apparatus for measuring the tear strength of an elastomer specimen as defined in claim 18 wherein said back support has a slot formed therein to accommodate said wire as said wire passes through said elastomer specimen.

20. An apparatus for measuring the tear strength of an elastomer specimen comprising a housing, said housing including a plurality of disc-shaped elements; means including one of said disc shaped elements for fixedly supporting said elastomer specimen; means supported by at least another one of said disc-shaped elements and in operable relationship to said elastomer specimen for applying a predetermined amount of force to said elastomer specimen; means operably connected to at least another of said disc-shaped elements for controlling the temperature of said elastomer specimen; and means connected to said force applying means for determining the resistance of said elastomer specimen to the application of said predetermined force whereby said tear strength of said elastomer can be measured with respect to a variation in the temperature of said elastomer specimen.

* * * * *